United States Patent [19]

Riddel

[11] 4,157,282

[45] Jun. 5, 1979

[54] METHOD FOR MAINTAINING STOICHIOMETRIC AIR/FUEL MIXTURES

[75] Inventor: John W. Riddel, Fenton, Mich.

[73] Assignee: General Motors Corporation, Detroit, Mich.

[21] Appl. No.: 825,597

[22] Filed: Aug. 18, 1977

Related U.S. Application Data

[63] Continuation of Ser. No. 524,674, Nov. 18, 1974, abandoned.

[51] Int. Cl.² ............................................. G01N 27/46
[52] U.S. Cl. .................. 204/1 T; 204/195 S; 123/119 E
[58] Field of Search ............................ 204/1 S, 195 S; 123/119 E

[56] References Cited

U.S. PATENT DOCUMENTS

| | | | |
|---|---|---|---|
| B 843,038 | 2/1976 | Sandler | 204/1 S |
| 3,768,259 | 10/1973 | Carnahan et al. | 204/195 S |
| 3,844,920 | 10/1974 | Burgett et al. | 204/195 S |
| 3,941,673 | 3/1976 | Takao et al. | 204/195 S |
| 4,005,001 | 1/1977 | Pebler | 204/195 S |

FOREIGN PATENT DOCUMENTS 2304464  8/1974  Fed. Rep. of Germany ....... 204/195 S

*Primary Examiner*—T. Tung
*Attorney, Agent, or Firm*—Robert J. Wallace

[57] ABSTRACT

A durable and relatively inexpensive air/fuel ratio sensor for detecting oxygen concentration in exhaust gases of internal combustion engines, that does not require a separate reference atmosphere. A body of stabilized zirconium dioxide with two opposite major faces serves as a solid oxygen ion electrolyte. A catalytic electrode is on one of the faces, while a noncatalytic electrode is on the other face. The body is mounted in an exhaust pipe so that both of the electrodes are exposed to the exhaust gases.

2 Claims, 8 Drawing Figures

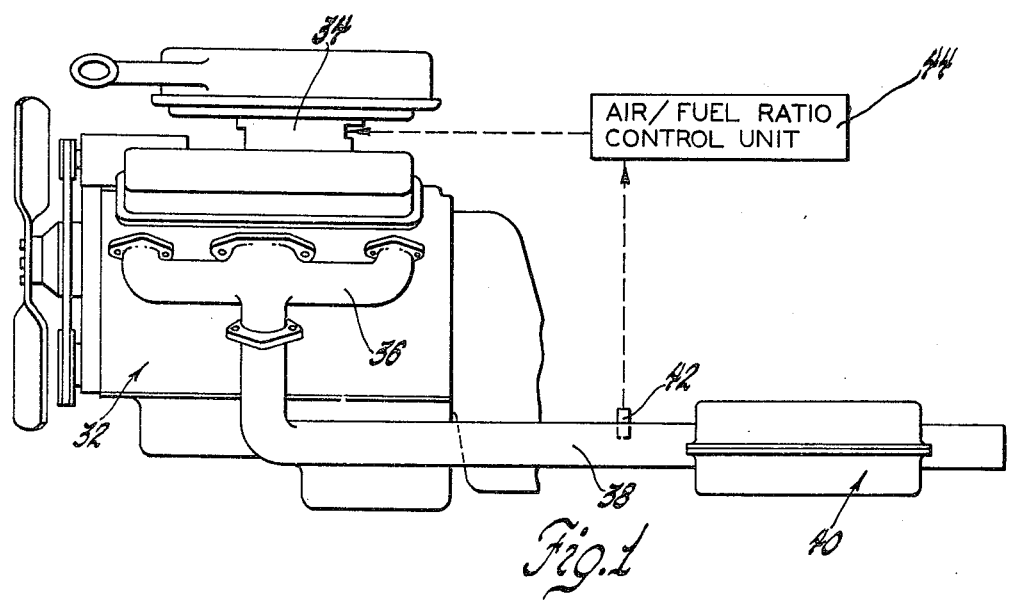
Fig. 1
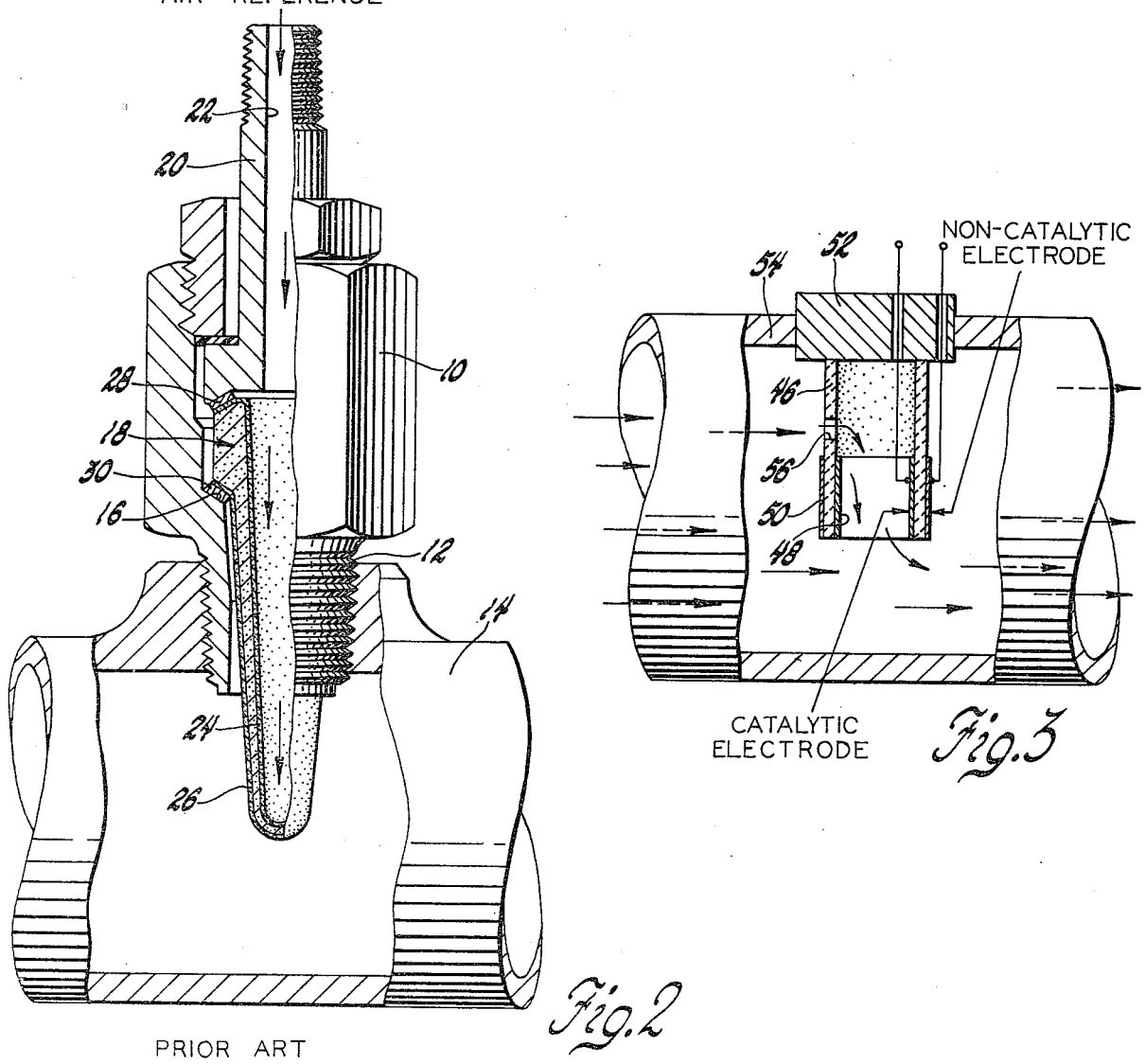
Fig. 2
PRIOR ART
Fig. 3

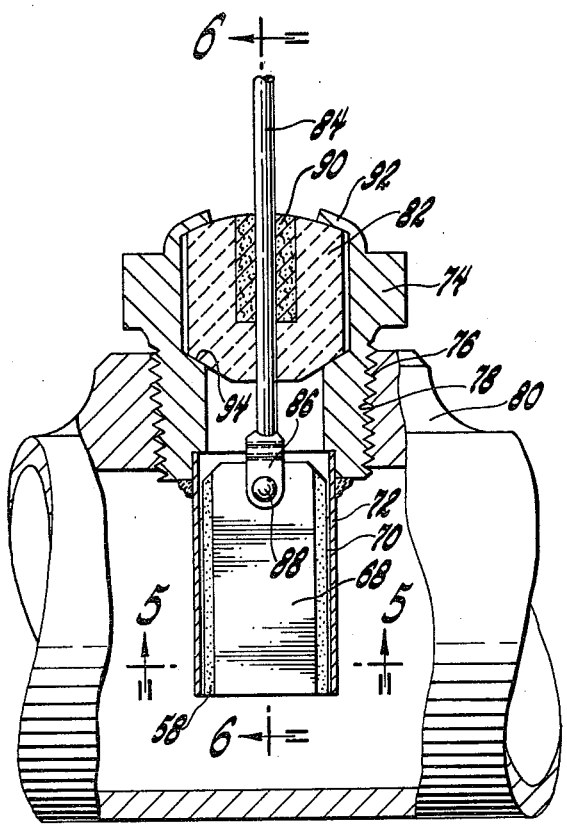

METHOD FOR MAINTAINING STOICHIOMETRIC AIR/FUEL MIXTURES

CROSS REFERENCE TO RELATED APPLICATION

This is a continuation of United States Patent application Ser. No. 524,674 now abandoned, entitled Air/Fuel Ratio Sensor Having Catalytic and Non-Catalytic Electrodes, filed Nov. 18, 1974 in the name of J. W. Riddel and assigned to the assignee of this application.

BACKGROUND OF THE INVENTION

This invention relates to an electrochemical cell for measuring oxygen concentration in a gas. More particularly, it relates to an air/fuel ratio sensor with a stabilized zirconium dioxide solid electrolyte that is incorporated in the exhaust system of an internal combustion engine.

A zirconia oxygen concentration cell has already been considered for use as an air/fuel ratio sensor for an automotive internal combustion engine. Such a sensor is shown in FIG. 2 and is labeled as "Prior Art". This sensor is disclosed in allowed United States patent application Ser. No. 417,724, entitled "Air/Fuel Ratio Sensor", Burgett et al, filed Nov. 21, 1973, and assigned to the same assignee as the present invention.

In this type of sensor, ambient air, which is used as a reference gas, bathes a catalytic reference electrode. Exhaust gases flowing from the engine bathe a sensing catalytic electrode. The sensor output, E(volts), is produced by movement of oxygen ions between the two catalytic electrodes in accordance with the Nernst equation:

$$E = -\frac{RT}{4F} \ln P_1/P_2$$

where
- R is the gas constant in joules/mole,
- T is the absolute temperature,
- F is the Faraday constant in coulombs,
- $P_1$ is the oxygen partial pressure of the air reference impinging the reference catalytic electrode, and
- $P_2$ is the oxygen partial pressure of the exhaust gas impinging the sensing catalytic electrode.

In lean air/fuel ratio regions, the oxygen partial pressure (concentration) in the exhaust gases significantly increases. It can increase to almost the partial pressure of air. In such instance, the ratio of partial pressures between the reference gas and the exhaust gases approaches unity, whereupon the output voltage of the sensor drops nearly to zero. When the air/fuel ratio is rich, the electrode exposed to the exhaust gases senses a low oxygen partial pressure. In this latter instance, the ratio of partial pressures becomes greater than one, whereupon there is a representative significant increase in output voltage of the sensor.

The oxygen concentration in the exhaust gases is a direct function of the air/fuel ratio entering the intake manifold of an internal combustion engine. Zirconia sensors have a unique characteristic in that they exhibit a drastic change in output voltage at about stoichiometric air/fuel ratios. It is generally accepted that improved engine performance is obtained at stoichiometric air/fuel ratios. Consequently, the output from the zirconia sensor can be used to control air/fuel metering systems at the carburetor and continuously adjust them to maintain the engine air/fuel mixtures at stoichiometric ratios.

The prior art type of device shown in FIG. 2 has provided extremely satisfactory results. However, two platinum catalyzed electrodes are used, and platinum is costly. Moreover, all of the air/fuel ratio sensors heretofore proposed have required a separate reference atmosphere, for example ambient air, for one of the catalytic electrodes. The reference gas catalytic electrode must be imperviously sealed from the exhaust gases, and vice versa. This requires somewhat complex design of the sensor housing, adds to cost, can decrease reliability, and so forth. Moreover, the zirconia element may crack under unusually adverse conditions. A crack may allow exhaust gases to mix with the reference gas, and consequently reduce the output of the sensor.

I have found a new and simple zirconia sensor construction that does not require two catalytic electrodes, does not require a reference gas, does not require electrode sealing and whose operation is not deleteriously affected by leaks through cracks in the zirconia body.

OBJECTS AND SUMMARY OF THE INVENTION

An object of this invention is to provide an improved method for maintaining stoichiometry in engine air/fuel mixtures by electrochemical analysis of exhaust gases.

Briefly, my invention involves regulating air/fuel ratio for an internal combustion engine to maintain stoichiometry in response to an output voltage from a zirconia-type oxygen sensor using non-equilibrium exhaust gases for reference. Catalytic and non-catalytic electrodes on opposite faces of a zirconia body are exposed to a single stream of non-equilibrium exhaust gases to produce the output voltage.

BRIEF DESCRIPTION OF THE DRAWINGS

FIG. 1 shows a schematic view of an automotive exhaust system that includes an air/fuel ratio sensor;

FIG. 2 shows an elevational view with parts broken away of a prior art sensor in an exhaust gas pipe;

FIG. 3 shows a diagrammatic view of a sensor made in accordance with this invention;

FIG. 4 shows an elevational view with parts broken away of one embodiment of the sensor of this invention;

FIG. 5 shows an enlarged fragmentary sectional view along the lines 5—5 of FIG. 4;

FIG. 6 shows an enlarged fragmentary sectional view along the lines 6—6 of FIG. 4;

FIG. 7 shows a sectional view along the lines 7—7 of FIG. 6; and

FIG. 8 shows a graph of the voltage output of the sensor of this invention vs. air/fuel ratio in an internal combustion engine.

DESCRIPTION OF THE PREFERRED EMBODIMENTS

FIG. 1 shows one example of an automotive system for controlling air/fuel ratio by means of an exhaust gas air/fuel ratio sensor. A prior art air/fuel ratio sensor is shown in FIG. 2. Briefly, this prior art device includes a hollow outer shell 10 that also includes threads 12 to mount the sensor in an exhaust pipe 14. Outer shell 10 includes a shoulder 16 for supporting an elongated cup-shaped stabilized zirconia oxygen sensing element 18. The zirconia element 18 is thin walled and has an enlarged rim that sealingly engages shoulder 16 on shell 10. A hollow tubular member 20, having an air inlet opening 22, locks the zirconia rim against shoulder 16. Zirconia element 18 includes inner and outer catalytic electrodes 24 and 26, respectively. Electrical connection is made to inner electrode 24 via a metal gasket 28 and inlet member 20. Analogously, electrical connection is made to outer electrode 26 via a similar metal gasket 30 through outer shell 10 to exhaust pipe 14.

The prior art device, as well as the air/fuel ratio sensor embodied in this invention, can be inserted into the automotive system shown in FIG. 1. Generally, the automotive system includes an internal combustion engine 32 that has fuel metering means, such as a carburetor 34. An exhaust manifold on engine 32 is connected to an exhaust pipe 38, which is in turn connected to a catalytic converter 40. The air/fuel ratio sensor designated by numeral 42 is mounted in exhaust pipe 38 upstream from catalytic converter 40. Sensor 42 is electrically connected to external circuitry such as air/fuel ratio control unit 44, which is in turn connected to carburetor 34. Control unit 44 includes suitable electronics for receiving the output of sensor 42 and means for regulating the adjustment of carburetor 34 in response to the output of sensor 42. In such a manner, the output of sensor 42 can be fed back to carburetor 34 to automatically maintain the air/fuel mixture emanating from carburetor 34 in a stoichiometric ratio.

FIG. 3 shows one embodiment of the sensor embodied in this invention. A hollow open ended tubular body 46 of stabilized zirconium dioxide serves as a solid oxygen ion electrolyte. The zirconia body 46 may be stabilized with materials such as calcia (CaO), magnesia (MgO), scandia ($Sc_2O_3$), or yttria ($Y_2O_3$). A gas previous catalytic electrode 48 coats the inner surface on the lower portions of tubular body 46. Catalytic electrode 48 is, for example, platinum. By catalytic electrode, I mean an electrically conductive coating on the zirconia body which promotes chemical oxidation of residual combustibles, such as carbon monoxide and hydrocarbons, in the exhaust gases. While platinum is preferred, other catalytic electrode materials which may be used include iron oxides and gold.

Coating the corresponding lower portions of the outer surface of tubular body 46 is a gas pervious noncatalytic electrode 50. In such manner noncatalytic electrode 50 is directly opposite catalytic electrode 48 on the inner walls of body 46. Noncatalytic electrode 50 may be, for example, silver. By non-catalytic electrode, I mean an electrically conductive coating on the zirconium dioxide body, which does not promote chemical oxidation of residual combustibles, such as carbon monoxide and hydrocarbons, in the exhaust gases with residual oxygen in the exhaust gases. This permits production of oxygen ions at the electrode-electrolyte interface directly corresponding to the actual residual oxygen concentration in the exhaust gases. While silver is preferred, it is believed that other noncatalytic materials, such as manganese, nickel, cobalt and their oxides, may also be used.

The upper portions of body 46 are attached to mounting member 52. Mounting member 52 is attached to the walls of exhaust pipe 54 so that body 46 extends inwardly into exhaust pipe 54, perpendicularly to the flow of exhaust gases designated by the arrows. Tubular body 46 includes an opening 56 exposed to the exhaust stream above electrodes 48 and 50. Opening 56 faces upstream so that the exhaust gases can enter opening 56 and flow through the inner portions of body 46 and out through its bottom as shown in FIG. 3. In such manner, the velocity of the exhaust gases is decreased as the gases pass over catalytic electrode 48. Similarly, catalytic electrode 48 is protected from direct impingement of the abrasive exhaust gases. In this embodiment, noncatalytic electrode 50 is not protected from direct impingement of the exhaust gases. However, noncatalytic electrode 50 is much more corrosion and abrasion resistant than the catalytic electrode 48. Consequently, protection of the noncatalytic electrode 50 is not required.

It should be emphasized that noncatalytic electrode 48 and catalytic electrode 50 are both exposed to the exhaust gases. This is contrasted with the prior art sensors such as that shown in FIG. 2. In the prior art sensor, the exhaust gases contact only electrode 26 whereas a separate reference gas, such as air, contacts electrode 24. Furthermore, both of the electrodes of such prior art sensors are made of expensive catalytic materials, such as platinum.

FIGS. 4 through 7 show another embodiment of the sensor of this invention. A generally rectangular plate 58 of stabilized zirconium dioxide serves as a solid oxygen ion electrolyte. Plate 58 includes two major parallel faces 60 and 62, with side portions 64 and 66. Noncatalytic coating 68 covers the major portion of face 60, yet it is spaced from side portions 64 and 66. Noncatalytic electrode 68 extends vertically the entire length of plate 58, as can be seen most clearly in FIGS. 4 and 6. Catalytic electrode 70 coats major face 64 and extends around onto side portions 64 and 66. Catalytic electrode 70 is spaced from the top portion of plate 58 as can be seen most clearly in FIGS. 6 and 7.

Plate 58 is press fitted longitudinally into a metal tubular sleeve 72. Sleeve 72 is open at its lower end. The upper end of sleeve 72 is welded to the lower portion of a circular housing member 74. Housing member 74 is made of steel, for example, and has threads 76 on its lower outer periphery for engaging the mounting threads 78 in an upstanding portion of exhaust pipe 80. In such manner, electrical connection is made between catalytic electrode 70 and exhaust pipe 80 which can be used as an electrical ground. A plug 82 made of electrically insulating material such as ceramic, fills the upper portion of the chamber defined by housing member 74. A conductor rod 84 extends coaxially through plug 82. The lower portion of rod 84 includes an S-bend 86 with a rivet 88 attached thereto. As can be seen most clearly in FIG. 6, rivet 88 extends through plate 58 and provides electrical connection between noncatalytic electrode 68 and rod 84. An insert 90 of asbestos or talc serves to insure a gas tight seal between plug 82 and rod 84. Lip portion 92 can be crimped so as to press plug 82 against shoulder portion 94 to provide a gas tight and rigid structure as shown in FIG. 4. While in this embodiment both noncatalytic electrode 68 and catalytic electrode 70 are protected from direct impingement of abrasive exhaust gases by sleeve 72, it should be emphasized that both electrodes remain in the same exhaust gas atmosphere since the bottom of sleeve 72 is open at its lower end.

FIG. 8 shows the voltage output of a sensor embodied in this invention as a function of air/fuel ratio. It is believed that the noncatalytic electrode allows oxygen molecules to pass through it to the noncatalytic electrode-electrolyte interface without any concurrent chemical oxidation of residual combustibles present in the exhaust gases. Therefore, the oxygen concentration at that interface, which is the situs of electrochemical reaction, is about the same as the oxygen concentration in the exhaust gases. On the other hand, the catalytic electrode promotes chemical oxidation of oxidizable constituents or residual combustibles, such as carbon monoxide and hydrogen, which may be present in the exhaust gases. Such a reaction lessens the concentration of oxygen in the exhaust gases by the time they reach the interface between the zirconium dioxide electrolyte and the catalytic electrode.

It should be emphasized that this invention recognizes that there is still a significant concentration of unreacted, residual, oxygen in the exhaust gases regardless as to the air/fuel ratios used. This unreacted oxygen is used as the reference gas for the noncatalytic electrode of this invention.

At lean air/fuel ratios, there is a relatively large amount of oxygen and small amounts of residual combustibles in the exhaust gases. Thus, a correspondingly relatively large amount of oxygen ions are produced at the noncatalytic electrode-electrolyte interface. Since there is very little residual combustibles which may be chemically oxidized by the catalytic electrode and thereby lessen the oxygen concentration at the catalytic electrode-electrolyte interface, an almost equal amount of oxygen ions are produced at that interface under equilibrium conditions. Accordingly, there is negligible ion exchange between the two electrodes, thus resulting in a small voltage output.

At rich air/fuel ratio mixtures, however, there is a smaller concentration of oxygen and a greater concentration of residual combustibles which may be oxidized in the exhaust gases. Consequently, a smaller amount of oxygen ions are produced at the noncatalytic electrode-electrolyte interface than with lean mixtures. However, an even smaller amount of oxygen ions are produced at the catalytic electrode-electrolyte interface. This is because under equilibrium conditions the catalytic electrode promotes chemical oxidation of the residual combustibles in the exhaust gases at rich air/fuel ratio mixtures. Accordingly, almost all of the oxygen at the catalytic electrode reacts with the residual combustibles to almost completely deplete the already small concentration of oxygen in the exhaust gases. This produces a significant differential of oxygen concentration sensed by the two electrodes. Therefore, oxygen ions are conducted from the noncatalytic electrode to the catalytic electrode thereby producing a responsive voltage output. As can be seen in FIG. 8, there is a drastic change in voltage at stoichiometric (14.7) air/fuel ratio mixtures. The sensor of this invention provides a voltage output differential of about 500 millivolts. Such a voltage can supply an output signal which may be fed back to a carburetor through an air/fuel ratio control unit to maintain the air/fuel ratio at stoichiometric. In such manner, improved engine performance is obtained.

It should again be emphasized that the air/fuel ratio sensor of this invention does not require a separate reference atmosphere as do prior art sensors. Furthermore, only one electrode need be catalytic. Accordingly, a much more durable and inexpensive air/fuel ratio sensor is provided by this invention.

I claim:

1. A method for maintaining internal combustion engine air/fuel mixtures at stoichiometry by electrochemical analysis of engine exhaust gases, using non-equilibrium oxygen content of exhaust gases from both rich and lean air/fuel ratios as a reference, comprising:
   forming a single stream of exhaust gases from an internal combustion engine intended to combust stoichiometric air/fuel mixtures, said single stream being from fuel-rich, fuel-lean and stoichiometric air/fuel mixtures and always non-equilibrated;
   directing said single stream simultaneously across two opposite major faces of a zirconium dioxide solid electrolyte body to establish an output voltage between catalytic and non-catalytic gas pervious electrodes respectively on said faces, based on non-equilibrium oxygen content in said exhaust gases as a reference atmosphere regardless as to the air/fuel ratio from which produced;
   generating an electrical control signal in response to said output voltage that is representative of a substantially stoichiometric air/fuel mixture to be introduced into said engine; and
   regulating air/fuel mixtures introduced into said engine in response to said electrical control signal.

2. A method for maintaining internal combustion engine air/fuel mixtures at stoichiometry by electrochemical analysis of engine exhaust gases, using non-equilibrium oxygen content of exhaust gases resulting from both rich and lean air/fuel mixtures as a reference, comprising:
   forming a single stream of exhaust gases from an internal combustion engine intended to combust stoichiometric air/fuel mixtures, said single stream being from fuel-rich, fuel-lean, and stoichiometric air/fuel mixtures and always non-equilibrated;
   directing said single stream simultaneously across two opposite major faces of a zirconium dioxide solid electrolyte body to produce an output voltage between gas pervious electrodes on said faces based on non-equilibrium oxygen content in said exhaust gas stream as a reference, the electrode on one of said faces catalyzing chemical oxidation substantially to equilibrium of unreacted exhaust gas combustibles and producing an electrode potential varying with the air/fuel mixture combusted, the electrode on the other face not catalyzing such chemical oxidation and producing an electrode potential not significantly varying with the air/fuel mixture combusted;
   generating an electrical control signal in response to said output voltage that is representative of a substantially stoichiometric air/fuel mixture to be introduced into said engine; and
   regulating air/fuel mixtures introduced into said engine in response to said electrical control signal.

* * * * *